April 13, 1937. J. A. ARMSTRONG Plant Pat. 243
ROSE
Filed Nov. 4, 1936
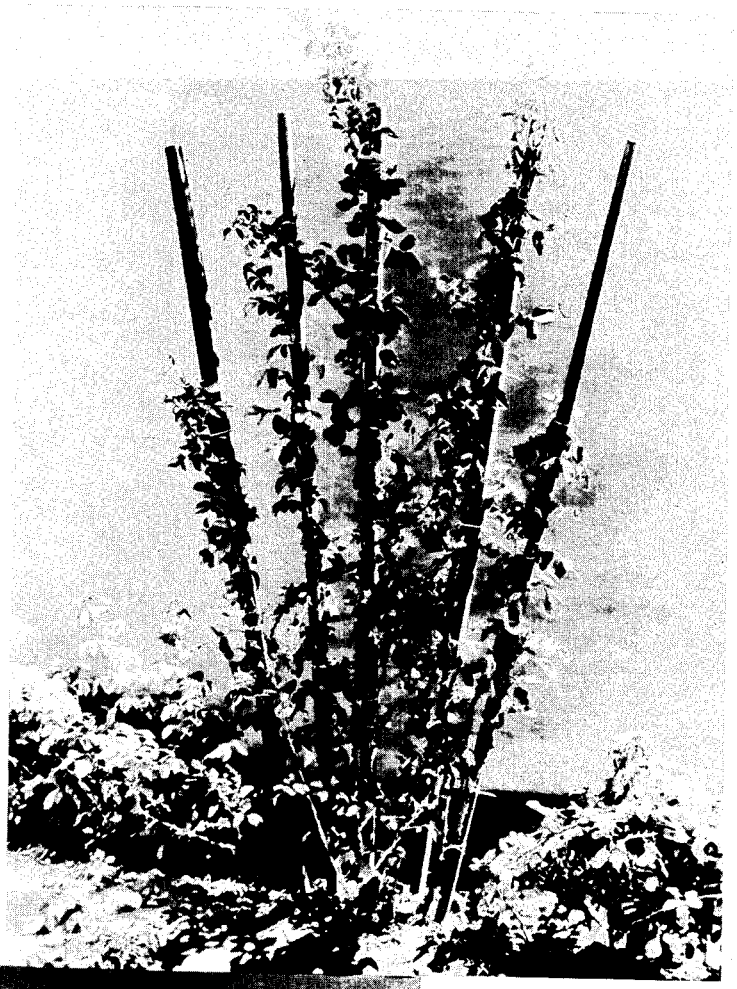
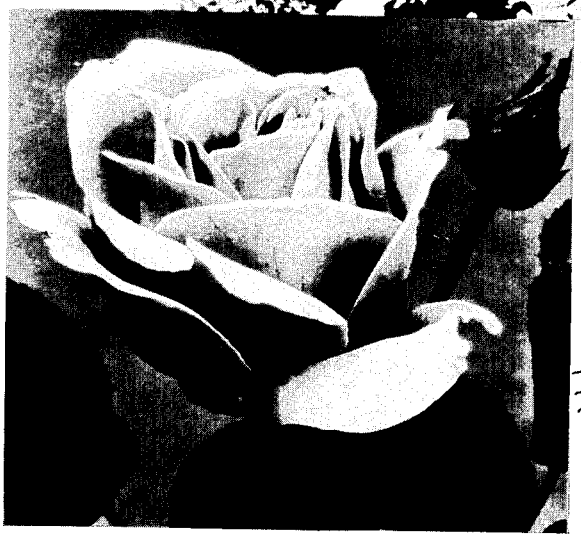
INVENTOR
John A. Armstrong
By Orville M. Kile
PLANT PATENT AGENT Patented Apr. 13, 1937

Plant Pat. 243

UNITED STATES PATENT OFFICE

243

ROSE

John A. Armstrong, Ontario, Calif., assignor to Armstrong Nurseries, Ontario, Calif.

Application November 4, 1936, Serial No. 109,173

1 Claim. (Cl. 47—61)

The present invention relates to a new and distinct variety of climbing rose, the distinctive feature being a vigorous climbing habit.

This new variety originated as a sport of Golden Dawn and closely resembles that variety in all respects except its growing habits and the size of the blossoms. It sends up stout, vigorous canes six to ten feet or more in length as distinguished from the bush Golden Dawn which usually attains no more than three or four feet in height.

Another growing habit which distinguishes this variety from Golden Dawn is the production of its largest burst of bloom in the spring with only scattered flowers throughout the rest of the blooming season, while the bush Golden Dawn blooms throughout the summer.

Because of the climbing habit and its ability to cover a great deal more space, the number of flowers appearing at once is multiplied many times in its main blooming season in the spring, as compared with the bush Golden Dawn.

The flowers on the climbing variety are usually larger than those borne on the bush Golden Dawn, and this feature combined with the vigorous growth and numerous flowers, makes it a very valuable variety for general planting.

The accompanying illustration shows the climbing growth of the new variety as compared with the bush variety at its base; also a view of opening flowers, stems and foliage.

Following is a more detailed description of this new variety.

*The plant*

*Foliage.*—Bronzy green; profuse and of splendid texture.

*Sepals.*—Only slightly foliaceous.

*Growth.*—Vigorous climber, sending up stout, vigorous canes some of which attain a length of more than ten feet; covers a great deal of space.

*Blooming habit.*—Has largest burst of bloom in the spring with occasional blooms throughout the remainder of the season. In the spring blooming season this variety has a great many more flowers at one time than does the bush Golden Dawn, and these flowers are usually larger as compared with those of the Golden Dawn.

*Disease resistance.*—Very resistant to diseases common to roses.

*The flower*

No novelty of color or character of flower is claimed. As above stated, the flower closely resembles Golden Dawn except that the size averages larger.

Bud:

*Shape.*—Ovoid.

*Size.*—Large.

*Color.*—Rich shade of sunflower yellow suffused with rose color, the same as the bush Golden Dawn.

*Peduncle.*—Covered with numerous spines.

Bloom:

*Size.*—Large and double, having 40 to 50 petals.

*Form.*—High centered but opening into cup shape when older.

*Color.*—Uniform lemon-yellow same as Golden Dawn.

*Texture.*—Petal texture very substantial.

*Fragrance.*—Notably delicious tea fragrance.

Having thus disclosed my invention, I claim:

The new variety of rose plant herein described and illustrated, characterized particularly by its vigorous climbing habit, its usual production of larger flowers as compared with those of the bush Golden Dawn, and its habit of producing most of its bloom in the spring and blooming intermittently throughout the remainder of the season rather than continuously as does the bush Golden Dawn.

JOHN A. ARMSTRONG.